United States Patent [19]

Van Compernolle

[11] Patent Number: 4,648,403

[45] Date of Patent: Mar. 10, 1987

[54] METHOD AND APPARATUS FOR PROVIDING SPREAD CORRECTION IN A MULTI-CHANNEL COCHLEAR PROSTHESIS

[75] Inventor: Dirk S. Van Compernolle, Palo Alto, Calif.

[73] Assignee: The Board of Trustees of the Leland Stanford Junior University, Stanford, Calif.

[21] Appl. No.: 734,500

[22] Filed: May 16, 1985

[51] Int. Cl.⁴ ............................................. A61N 1/30
[52] U.S. Cl. ............................................... 128/419 R
[58] Field of Search ................... 128/419 R, 421–423, 128/784–786; 179/107 R, 107 FD, 107 BC

[56] References Cited

U.S. PATENT DOCUMENTS

| | | | |
|---|---|---|---|
| 4,188,667 | 2/1980 | Graupe et al. | 179/107 FD |
| 4,284,085 | 8/1981 | Hansen et al. | 128/784 |
| 4,400,590 | 8/1983 | Michelson | 179/107 FD |
| 4,403,118 | 9/1983 | Zollner et al. | 179/107 FD |
| 4,495,384 | 1/1985 | Scott et al. | 179/107 FD |
| 4,495,917 | 1/1985 | Byers | 128/419 R |
| 4,510,936 | 4/1985 | Fourcin et al. | 128/419 R |
| 4,515,158 | 5/1985 | Patrick et al. | 128/419 R |
| 4,532,930 | 8/1985 | Crosby et al. | 128/419 R |
| 4,536,844 | 8/1985 | Lyon | 128/419 R |

FOREIGN PATENT DOCUMENTS 2823793 9/1979 Fed. Rep. of Germany ... 128/419 R

OTHER PUBLICATIONS dMerzenich et al., "Cochlear Implant Prostheses: Strategies and Progress", *Annals of Biomedical Engineering*, vol. 8, Jun. 1981, pp. 361–368.

Hochmair-Desoyer et al., "An Eight Channel Scala Tympani Eletrode for Auditory Prostheses", *IEEE Trans BME*, vol. BME-27, No. 1, Jan. 1980, pp. 44–50.

Douek et al., "A New Approach to the Cochlear Implant", *Proc Roy Soc Med*, vol. 70, Jun. 1977, pp. 379–383.

Primary Examiner—William E. Kamm
Assistant Examiner—Mitchell J. Shein
Attorney, Agent, or Firm—Flehr, Hohbach, Test, Albritton & Herbert

[57] ABSTRACT

By using a deconvolution technique, the outputs of a speech processor to the electrodes, based on current spread curves, the proper outputs of each eletrode are determined to provide the desired stimulation of the nerves. It has further been found that either overestimation or underestimation of the problem will result in improper stimulation and, in fact, a diminished accuracy of stimulation of the nerve rather than enhanced stimulation.

Thus, the method relies on an inverse convolution of what amounts to the known desired stimulation of the auditory nerves to determine what information should be provided at the electrodes which are connected to the output channels of the stimulator system. By analysis of these deconvolution techniques, instead of having a range of positive stimulations of the electrodes to produce the output spread curves, some positive and some negative stimulation of these output electrodes will be necessary to produce the proper range of stimulation and the necessary peaks and slopes of a desired curve to represent a desired sound pattern.

7 Claims, 6 Drawing Figures

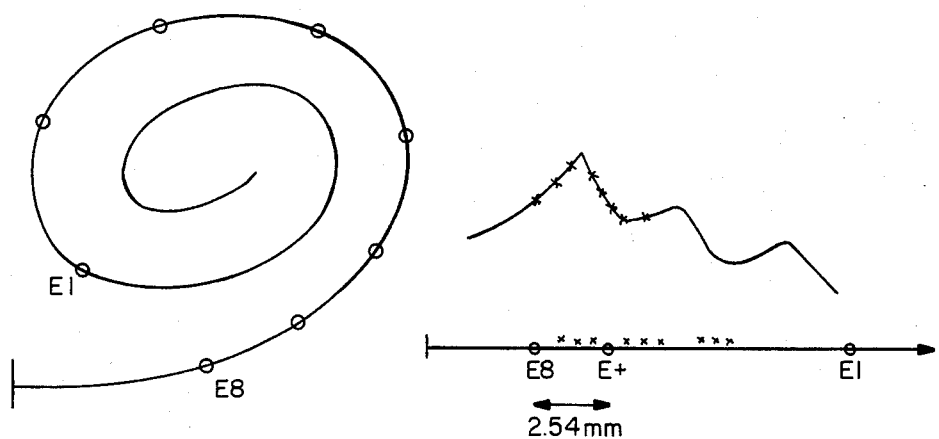
FIG. — 1
$$\frac{d}{(x^2+d^2)} = \frac{d}{\sqrt{x^2+d^2}} \cdot \frac{1}{\sqrt{x^2+d^2}}$$
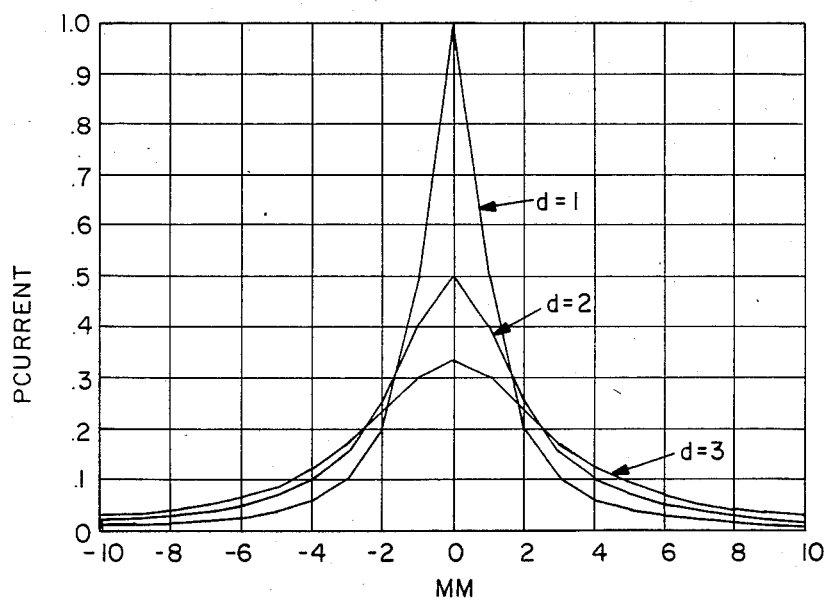
FIG.—2

FIG.—4

METHOD AND APPARATUS FOR PROVIDING SPREAD CORRECTION IN A MULTI-CHANNEL COCHLEAR PROSTHESIS

FIELD OF THE INVENTION

The present invention was developed under NIH Grant No. NS 10532-12 the U.S. Government enjoys rights in the disclosed invention pursuant to this grant.

This invention is directed generally to the field of medical electronics and more particularly to a method and apparatus for compensating for current spreading in a cochlear prosthesis.

CROSS-REFERENCE TO RELATED APPLICATIONS

The present application incorporates by reference applications entitled, "A Multi-Channel Implantable Neural Stimulator," filed Apr. 2, 1985, under Ser. No. 719,231, now U.S. Pat. No. 4,592,359, invented by Douglas C. Galbraith, and "A Wide Band Inductive Transdermal Power and Data Link," Ser. No. 719,232 filed Apr. 2, 1985, invented by Douglas C. Galbraith filed concurrently herewith.

BACKGROUND OF INVENTION

The above two applications and the present invention are directed to the problems of profoundly deaf individuals; i.e., people whose hearing loss is greater than 90 db. For most, no surgery or other treatment exists that can restore their hearing. These inventions, and especially the present invention, are directed to an auditory prosthesis which electrically stimulates neural tissue producing the sensation of sound and restoring hearing to the profoundly deaf.

An auditory prosthesis system consists essentially of four parts; the speech processing hardware, the power and data transmitter, the implanted receiver stimulator, and the implanted electrodes. The external electronics to perform the speech processing are the subject of a separate body of technology and are not part of this application. The coupling of the skin is achieved using the incorporated application entitled "A Wide Band . . . . . " This system takes the digitally encoded signals and transmits them along with power through the skin and into the implanted stimulator. The stimulator, disclosed in the incorporated "Multi-Channel Implantable . . . " decodes the bidstream and delivers charge or current wave forms into electrodes implanted in the auditory nerve or cochlea.

The cochlea itself and the cochlear prosthesis are in the shape of a snail, with the electrodes which are to transmit sound to the auditory nerve spaced along the prosthesis. In fact, the prosthesis lies in the lower chamber of the cochlea called the scala tympany.

The nerves are located in this chamber, which is a liquid filled chamber, and the nerves are separated from this chamber by a bony wall. The objective is to stimulate these nerves with the current from the electrodes.

The cochlea is laid out in what is called a tonotopic fashion, i.e., the nerves at one end bringing up high frequencies and at the opposite end picking up the lower frequencies. Therefore, the objective of the cochlear prosthesis is to extend it and its electrodes along where the nerves are tonotopically organized, and stimulate the appropriate nerve to represent sounds at different frequencies. It would be hoped that by energizing a particular electrode, the adjacent nerves are stimulated to provide an inherent frequency sorting. However, in reality this ideal situation does not actually prevail due to a phenomenon called current spreading, whereby activation of any electrode will in fact stimulate many of the electrodes at a distance from the activated electrode. Not all the nerves are stimulated to the same degree, but there is not a great deal of difference.

Therefore, it is an objective of the present invention to provide an improved means of stimulating the auditory nerves in an auditory prosthesis system.

More particularly, it is an objective of the present invention to provide an improved system and method for auditory stimulation which overcomes the current spreading problem.

SUMMARY OF THE INVENTION

In summary the invention comprises the recognition, not previously made in this field, that having recognized the problem of current spreading, a solution lies not in directly applying the outputs of a speech processor to the electrodes, but by using a deconvolution technique on these outputs based on the current spread curves, to determine what should be the proper outputs of each electrode to provide the desired stimulation of the nerves. It has further been found that either overestimation or underestimation of the problem will result in improper stimulation and, in fact, a diminished accuracy of stimulation of the nerve rather than enhanced stimulation.

Thus, the method relies on an inverse convolution of what amounts to the known desired stimulation of the auditory nerves to determine what information should be provided at the electrodes which are connected to the output channels of the stimulator system. It has further surprisingly been found by analysis of these deconvolution techniques that in fact instead of having a range of positive stimulations of the electrodes to produce the output spread curves, in fact some positive and some negative stimulation of these output electrodes will be necessary to produce the proper range of stimulation and the necessary peaks and slopes of a desired curve to represent a desired sound pattern.

BRIEF DESCRIPTION OF THE INVENTION

The subject invention will be clearly understood by a study of the following detailed disclosure which analyzes the development of the present invention with reference to the accompanying figures wherein FIG. 1 illustrates a cochlear prosthesis used to achieve auditory stimulation, and illustrates the auditory stimulation achieved with known systems;

FIG. 2 shows neural excitation for different amounts of current spreading as performed in prior art systems;

DETAILED DESCRIPTION OF THE DRAWINGS

Figure 3:
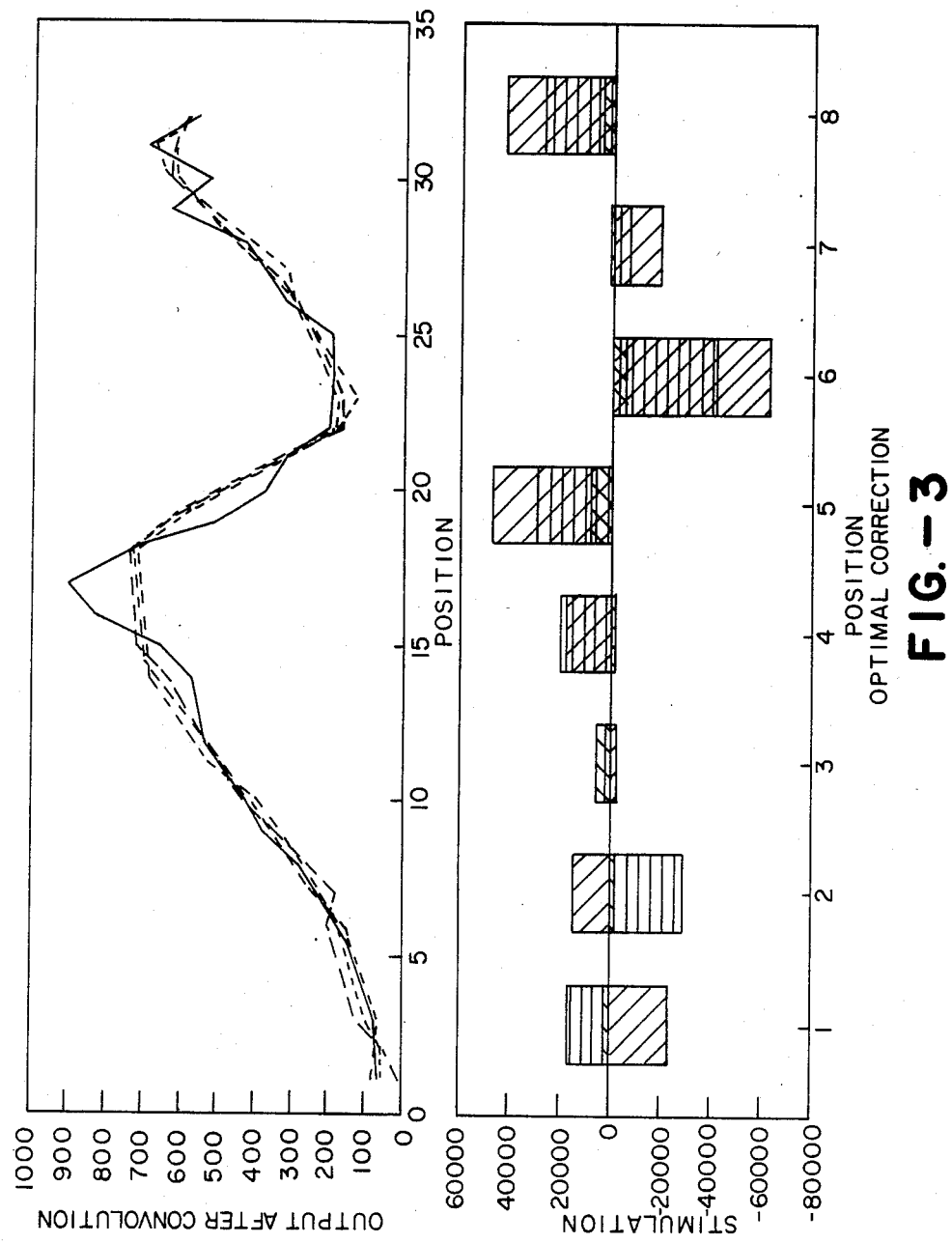
FIG. 3 shows optimal excitation patterns for known current spreads, and the desired excitation pattern of various electrodes to achieve optimal excitation.

As the firing rate of an auditory nerve is roughly proportional to the intensity of the electrical stimulus, the goal for a cochlear prosthesis can be formulated as that of presenting a current pattern to the nerve which matches as well as possible the pattern of neural activity which would be generated by a normal cochlea.

Most of the mathematics that are used will equally apply for a 3-D or 2-D stimulation. A simplified 2-D model with an unrolled cochlea as shown in FIG. 1B is used throughout. The major assumption made is that effect of currents can be represented by a single number and that no vector representation is necessary. The prosthesis is assumed to be located in a perfectly resistive medium, and hence no phase representation is necessary. Under these assumptions currents will add simply as scalers.

From the mathematics involved it will become obvious that not the absolute distances but rather *distances as spacings between electrodes* is the basic unit. For convenience a new unit of length the 'el,' i.e., the distance between two adjacent electrodes is used. In many cases it will also be necessary to use a finer scale, the 'gel,' which is one quarter of an el.

It will be convenient, from a bookkeeping point of view, to have one single number referring to the amount of spread (for a certain type of spread function), the 'degree.' The degree is the number of els up to where current spread is measurable. Some arbitrary threshold for detection must be chosen for current spread functions that only go asymptotically to 0. For linearly decreasing spread functions the degree is the (projected) distance from stimulation where the absolute value of current spread becomes 0. "Degree" also refers to the mathematical description of a certain spread function and to the correction functions that will be introduced later.

Experiments with patients have shown that "linearly decreasing" current spread curves fit the physical reality well and are sufficiently correct approximations of the physical spread curves for the application of the present invention.

Current spread can most simply be represented by a convolution of the input (electrode currents) with a spread function. However, for a number of reasons which will become clearer further on, it will be convenient to switch to a different representation from the beginning.

One can write a convolution as a multiplication with a banded matrix, in which the band is the spread function. This representation is much more flexible as it allows us to depart from an exact convolution. Different spread functions for different electrodes can be used, the number of outputs is independent of the number of inputs and other effects than the current spread alone could be added in. Thus:

|  |  | output = conv*stim |  |  |  |
|---|---|---|---|---|---|
| conv = | a | 0 | 0 | 0 | ... |
|  | b | 0 | 0 | 0 | ... |
|  | c | a | 0 | 0 | ... |
|  | 0 | b | 0 | 0 | ... |
|  | 0 | c | a | 0 | ... |
|  | 0 | 0 | b | 0 | ... | where stim is the stimulation vector, output is the neural excitation pattern and conv is a banded matrix.

Assume the output of an auditory model, yielding the desired neural excitation pattern, is available. This function will be shown as a full line in the FIGS. 2–6 and will be referred to as "input." This input has been sampled at 32 points, assumed directly opposite of the electrode array, i.e., E1 is assumed opposite of the middle of points 2 and 3 in the input; E8 is assumed opposite of midway point 30–31 on the input. The used layout is illustrated below.

| E1 |  |  |  | E2 |  |  |  | ... |  | E8 |  |
|---|---|---|---|---|---|---|---|---|---|---|---|
| I1 | I2 | I3 | I4 | I5 | I6 | I7 | I8 | ... | I30 | I31 | I32 |

As a first case, the effect of neglecting the current spread effect the best estimate of desired current is applied to the electrodes without any transformation. A simple summation of 4 adjacent values was used to reduce the 32 element input vector to an 8 element stimulation vector. FIG. 2 shows the resulting neural excitation for different amounts of current spread. Degrees 2, 4 and 6 were used.

The figure is self-explanatory. Almost all spectral features are lost, due to smoothing. Only in the case of degree 2 there is a very limited amount of spectral coloring left, but this is too optimistic for a typical cochlear prosthesis.

The example shows that "neglecting" current spread is a horrible heuristic. However, it is the only one that has been used in the past. That averaging values is not the way to go to compensate for a smoothing effect is well known. To a large extent the problem is similar to the blurring that occurs in imaging systems, however much more severe.

The solution that is applied here is a generalized convolution scheme (with different current spread functions for different electrodes). Knowing the relationship between "stim" and "output" this invention provides the "stim" that will yield the best approximation to "input." No exact solution is possible as the set of equations is overdeterminated. This overdetermination would not be necessary if one would limit the number of observation points (size of input and output) to the number of electrodes, but it was built in on purpose. In the deterministic case, an exact inverse of the convolution matrix could be obtained, and using this correction would yield perfect values directly opposite of the electrodes, but severe transients in between would have to be tolerated. Overdetermination describes the spectrum more precisely, and this is welcome as 8 (number of electrodes) values is in general a minimal representation of a spectrum.

The optimum stim-vector is obtained by multiplying "input" with the pseudo-inverse of "conv," "dcnv." The set of relevant equations for this least squares problem can be written as:

$$dcnv = pinv\ (conv)$$

$$stim\_o = dcnv*input$$

$$output\_o = conv*stim\_o$$

$$output\_o = conv*(dcnv*input)$$

The application of the pseudo-inverse is only possible with our original assumptions of linearity and superposition of currents. The pseudo-inverse of conv, the "deconvolution matrix," only has to be computed once and is independent of the desired neural excitation pattern.

In the stimulation that follow, linear spread patterns of different degrees are used to explore the effects of both overestimating or underestimating the degree of the spread function.

FIG. 3 shows in the top part of the optimal approximation for different amounts of current spread (degree 2, 4 and 6) under the assumption that the current spread function is known exactly. In all cases the details at the basal end, which are more fine than one el, are lost; and also in all cases a sharp peak in the input function is not achieved. What is striking, however, is that there is hardly any difference in the resulting excitation patterns due to such large differences in current spread. The limiting factor seems to be the number of stimulation points. Very large differences do occur in the requested currents in order to obtain these excitation patterns. The necessary currents are shown in the lower part of FIG. 3. In absolute terms the following differences were found:

| spread (in els) | Requested Current 1-norm (arbitrary units) | absolute value (arbitrary units) |
|---|---|---|
| 1 | .13 | .03 |
| 2 | .32 | .09 |
| 3 | .96 | .24 |
| 4 | 1.73 | .41 |
| 5 | 1.81 | .50 |
| 6 | 2.32 | .63 |
| 7 | 2.40 | .87 |
| 8 | 3.11 | 1.14 |

Except for very minimal spread, bipolar stimulation in the longitudinal sense is necessary for sharpening of the current peaks.

Figure 4:
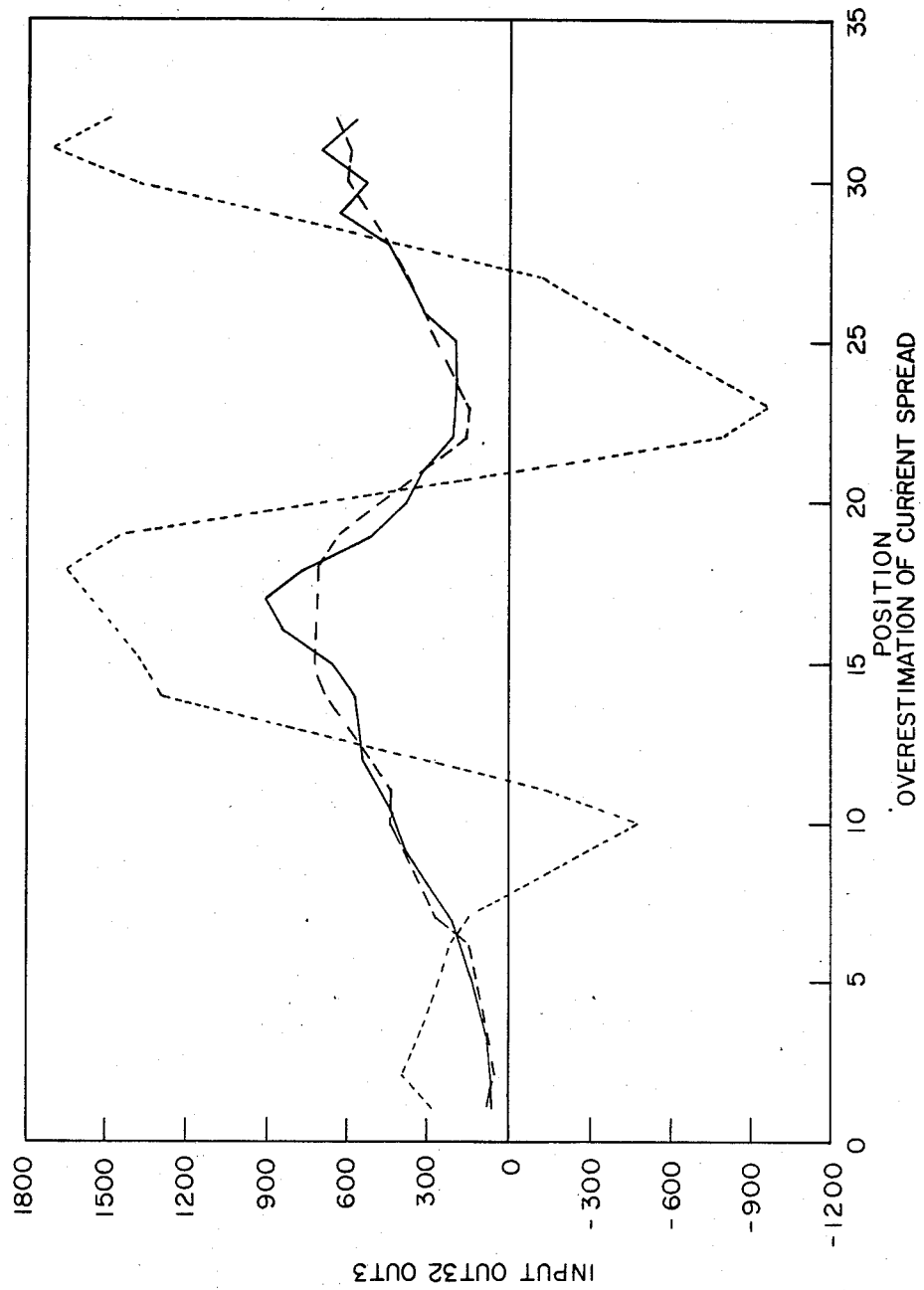
FIG. 4 shows the results of overestimation of current spreading.

As previously shown, the optimal stimulation patterns are drastically different from a smoothed version of the desired pattern, which has been used as zeroth order approximation. This definitely raises the question: "What happens if we over/underestimate the amount of current spread?" In the case of overestimation, the sharpening effect will be much more pronounced than what we intend it to be. The effect of overestimating only one degree is shown in FIG. 4. We see that we lose total control of the amplitude function with even strong phase reversals. Using an overestimated current spread function should be avoided, as intolerable current levels may result from it and the final result may even be worse than neglecting the current spread problem.

Figure 5:
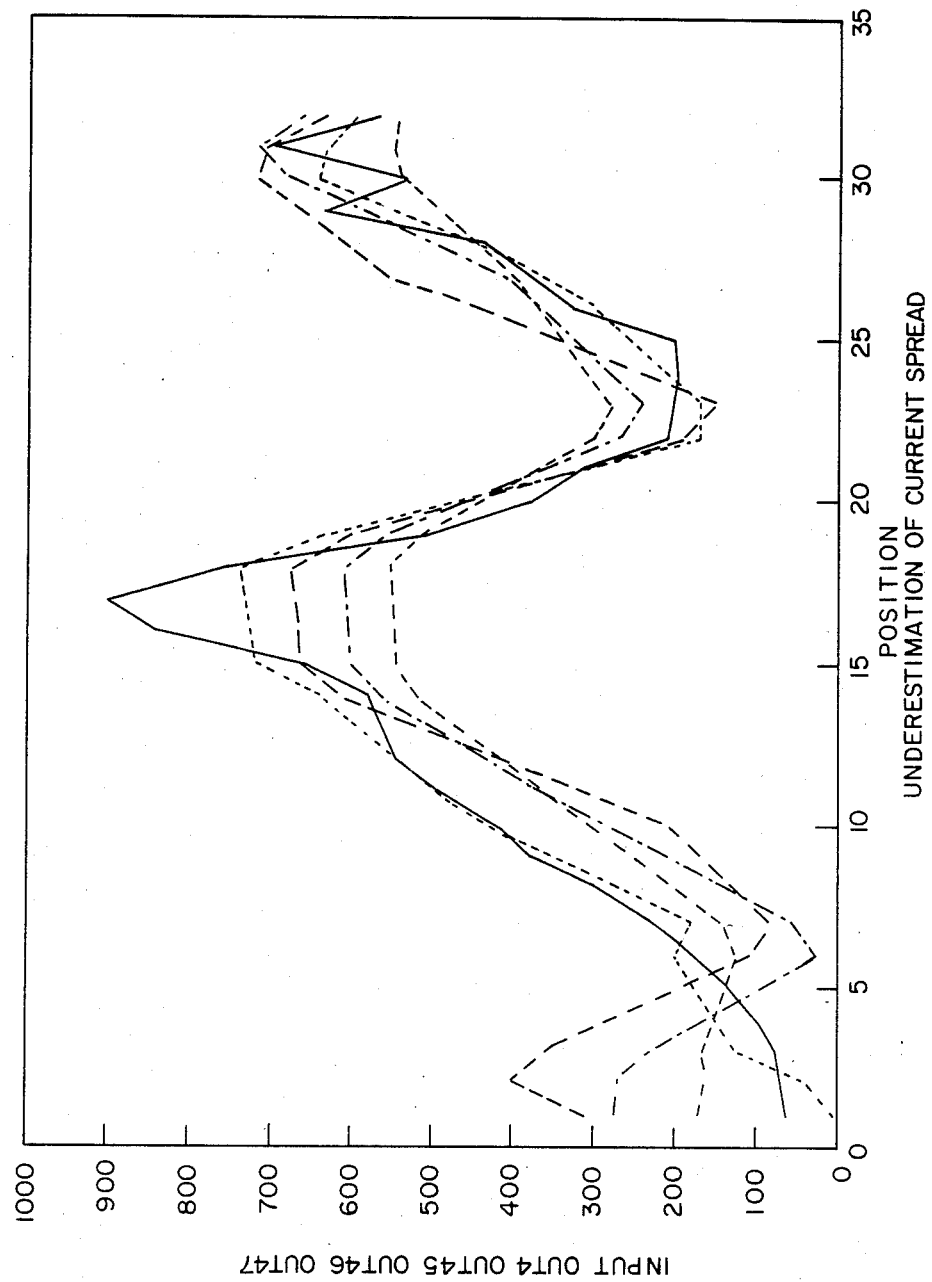
FIGS. 5 and 6 show the results of underestimation of current spreading.
Figure 6:
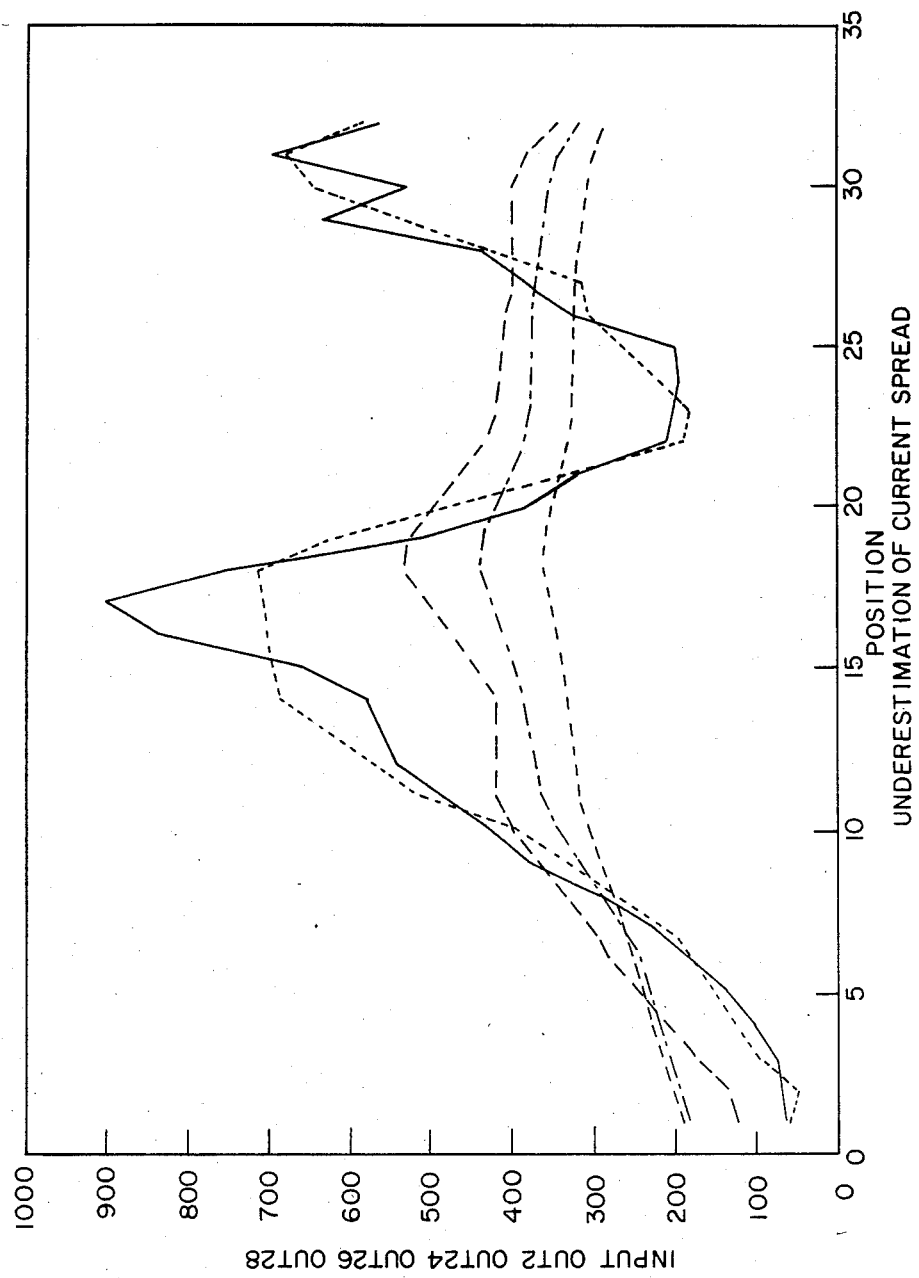

Underestimation of current spread is totally different than for overestimation, as this is in between neglecting the problem and the optimal correction. The resulting excitation patterns are medium smoothed. FIG. 5 shows the case where only a small correction is applied but where the actual spread varies from small degrees up to 8. In the latter case we see little difference with the results obtained from neglecting current spread. FIG. 6 shows results for cases where the discrepancies between anticipated spread and actual spread are less. Degradation is gradual. We can also observe the appearance of an extraneous peak in some of the stimulations. But even when a 4th degree correction is used for an actual 7th degree spread, we can clearly distinguish the two major peaks and the final result is much better than neglecting a 2nd degree spread.

From the preceding experiments we can deduce some strong recommendations on what degree of deconvolution to use. From the first experiment it is clear that even minor current spread (2 els) will introduce larger distortion, so in all cochlear prostheses one should account for the convolution introduced by the current spreading effect.

This convolution effect has largely been neglected up to now. Instead one applied the desired pattern immediately to the electrodes. As was shown, this produces a single broad peak after convolution for almost any speech-like sound. The differences between stimulation patterns and observed current distribution are such that in order to create localized peaks stimulation with opposite phases on adjacent electrodes is a necessity.

Another important advantage of deconvolution is that this approach lends itself to using a cochlear model with a number of channels that by far exceeds the number of electrodes. The spreading effect can then even be used to advantage as, using it, one can induce peaks in the observed current distribution with better resolution than the distance between the electrodes. Starting with a large number of channels (e.g., 32) and only reducing this number in the deconvolution stage will yield much better resolution than lumping the channels together in the initial spectral analysis.

Thus, the application describes an interface necessary between the existing cochlear models and the electrical stimulation pattern for a cochlear prosthesis. The approximation to the desired current distribution at the nerve endings can be greatly improved by using a cochlear model with a number of channels that exceeds the number of available electrodes and by accounting for the current spreading effect.

The current spread should definitely not be overestimated, which sets an upper boundary for the degree of the optimal deconvolution to be used. The effect of underestimating is not a function of the absolute underestimation but rather a function of the relative underestimation. The data on requested currents is also an incentive to use the deconvolution of the lowest possible degree. Combining all these factors leads to the conclusion that one should use a degree of deconvolution which corresponds to an underestimate of the current spread of 20-40%. The final choice will depend on how accurate the available current spread measurements are assumed to be and what the physical limits for current delivery are.

What is claimed:

1. A method for accurately stimulating the auditory nerves to a human comprising the steps of extending a cochlear prosthesis including a plurality of electrodes along a region where said nerves are tonotopically organized to detect both high and low frequencies, utilizing a speech processor to develop a desired set of stimulating currents for said nerves, and modifying said set of stimulating currents by an inverse convolution prior to their application to said cochlear prosthesis electrodes, whereby effects of current spreading are taken into account.

2. A method as in claim 1 wherein said inverse convolution is applied in a manner to provide positive stimulation of some of said electrodes and negative stimulation of the remainder of said electrodes.

3. A method as in claim 1 wherein said speech processor calculates signals for a number of output channels exceeding the number of electrodes, and including the step of reducing said excess number of outputs to equal the number of electrodes in the inverse convolution step of the process.

4. A method as in claim 1 wherein the step of developing said inverse convolution includes the step of totally eliminating overestimation of current spreading effects from said electrodes.

5. A method as in claim 1 wherein said inverse convolution is applied while underestimating current spreading effects from said electrodes.

6. A method as in claim 4 wherein said speech processor calculates a number of output channels exceeding the number of electrodes, and reducing said excess number of outputs to equal the number of electrodes in the inverse convolution step of the process.

7. A method as in claim 6 wherein said speech processor calculates a number of output channels exceeding the number of electrodes, and reducing said excess number of outputs to equal the number of electrodes in the inverse convolution step of the process.

* * * * *